United States Patent [19]

Dorner et al.

[11] Patent Number: 4,946,677

[45] Date of Patent: * Aug. 7, 1990

[54] PREPARATIONS ACTIVE AGAINST PSEUDOMONAS AERUGINOSA INFECTIONS AND METHODS OF PRODUCING THEM

[75] Inventors: Friedrich Dorner; Johann Eibl, both of Vienna, Austria

[73] Assignee: Immuno Aktiengesellschaft für Chemisch-Medizinische Produkte, Vienna, Austria

[*] Notice: The portion of the term of this patent subsequent to May 16, 2006 has been disclaimed.

[21] Appl. No.: 63,094

[22] Filed: Jun. 17, 1987

[30] Foreign Application Priority Data

Jun. 24, 1986 [AT] Austria .................................. 1716/86

[51] Int. Cl.$^5$ ........................ C07K 3/02; C07K 15/04; A61K 35/74; A61K 39/104
[52] U.S. Cl. ........................................ 424/92; 424/88; 514/2; 514/8; 514/21; 530/350; 530/395; 530/403; 530/806; 530/825
[58] Field of Search .................... 424/92, 89; 530/395, 530/389, 806, 825, 350; 514/2, 8, 21

[56] References Cited

U.S. PATENT DOCUMENTS

| | | | |
|---|---|---|---|
| 3,674,863 | 7/1972 | Fisher et al. | 424/92 |
| 3,928,565 | 12/1975 | Homma et al. | 424/92 |
| 3,983,229 | 9/1976 | Relyveld | 424/92 |
| 3,987,164 | 10/1976 | Homma et al. | 424/92 |
| 4,075,321 | 2/1978 | Relyveld | 424/92 |
| 4,079,126 | 3/1978 | Homma et al. | 424/92 |
| 4,298,597 | 11/1981 | Acres et al. | 424/92 |
| 4,693,891 | 9/1987 | Collins et al. | 424/87 |
| 4,702,910 | 10/1987 | Fukuda et al. | 424/92 |
| 4,774,086 | 9/1988 | Quenten-Millet et al. | 424/92 |
| 4,831,121 | 5/1989 | Montie et al. | 530/350 |

FOREIGN PATENT DOCUMENTS

8603974 7/1986 PCT Int'l Appl. .

OTHER PUBLICATIONS

Ansborg et al, J. Clin. Micro, 20(1), 84–8, (1984).
Freeman, Chapter 25, Textbook of Microbiology, 22nd Ed., (Saunders, Philadelphia), pp. 544–549.
Holder et al, Infect. Imm, 35(1), 276–80, (1982).
Jolles et al (Edtrs), in Molecular Biol. Biochem. Biophys, vol. 13, "Chemical and Biological Basis of Adjuvants", pp. 110–115, (1973).
Flagella Specific H Antigenic Schema of Pseudomonas aeruginosa Rainer Ansorg, Zbl. Bakt, Hyg., I. Abt. Orig. A 242, 228–238 (1978).
Immunological and Electrophoretic Characterization of Flagellins of Different H-Types of Pseudomonas aeruginosa, R. Ansorg and W. Schmitt, Med Microbiol Immunol, 168, 217 226 (1980).
Ion Exchange Chromatography and Gel Filtration, J. L. Fahey & Elizabeth W. Terry, Handbook of Experimental Immunology, Chapter 8.
Salt Fractionation of Immunoglobulins, K. Heide & H. G. Schwick, Handbook of Experimental Immunology, Chapter 7.
Loss of Virulence Associated with Absence of Flagellum in an Isogenic Mutant of Pseudomonas aeruginosa in the Burned-Mouse Model, Montie et al., Infection and Immunity, Dec. 1982, pp. 1296–1298.
Flagellar Preparations from Pseudomonas aeruginosa: Isolation and Characterization, Montie et al., Infection and Immunity, Jan. 1982, pp. 281–288.
Electrophoretic Separation and Molecular Weight Characterization of Pseudomonas aeruginosa H.-Antigen Flagellins, Allison et al., Infection and Immunity, Sep. 1985, pp. 770–774.

Primary Examiner—Margaret Moskowitz
Assistant Examiner—Jeff Kushan
Attorney, Agent, or Firm—Burns, Doane, Swecker & Mathis

[57] ABSTRACT

Preparations active against *Pseudomonas aeruginosa* Infections, namely vaccines for active immunization as well as preparations containing antibodies and destined for passive protection; as well as methods for the production thereof.

The vaccines contain protective flagellar (H) antigens of the serotype a and b, which consist of monomeric components, each monomeric component is composed of certain amino acids having a certain N-terminal amino acid sequence and has a certain molecular weight. The vaccines are made from purified flagellar (H) antigen solutions. The immunoglobulin-G-containing preparations contain flagellar (H) antibodies obtained from the blood plasma of human donors or mammals immunized with protective flagellar (H) antigens. They can be purified by methods of affinity chromatography.

7 Claims, No Drawings

PREPARATIONS ACTIVE AGAINST PSEUDOMONAS AERUGINOSA INFECTIONS AND METHODS OF PRODUCING THEM

The invention relates to preparations active against *Pseudomonas aeruginosa* infections. In particular, the invention relates to vaccines that contain protective *Pseudomonas aeruginosa* flagellar (H) antigens, which are destined for active immunization, as well as to immunoglobulin-G-containing preparations active against bacterium *Pseudomonas aeruginosa* infections, which are destined for passive protection.

The bacterium *Pseudomonas aeruginosa* is an opportunistic pathogenic organism which often occurs with hospital infections, mainly in patients having an impaired immune defense, such as patients suffering from burns, persons suffering from cystic fibrosis or having defective organic functions, and in tumor patients. Antibiotics are active against Pseudomonas infections only to a limited extent due to the occurrence of resistances, and therefore attempts have been made to find immunological methods for fighting infections caused by *Pseudomonas aeruginosa*.

Infections may be triggered by a variety of strains producing O-group antigens and H-antigens. According to the H antigen pattern according to Ansorg (Zbl. Bakt. Hyg. I. Abt. Orig. A 242, 228–238 (1978)), with *Pseudomonas aeruginosa* it is differentiated between a complex flagellar (H) antigen a having the partial antigens $a_0, a_1, a_2, a_3, a_4$ and a uniform flagellar (H) antigen b, by using the indirect immunofluorescence technique. The partial factors $a_0$–$a_4$ are independent determinants, so that a flagellar antigen pattern having several H-types results. O-groups and H-type show free combinations.

Strains used for preparing *Pseudomonas aeruginosa* bacterial cultures and the antigens produced are listed in the following Table 1.

TABLE 1

|   | Strain | H-type |
|---|--------|--------|
| 1 | 170001 | b |
|   | M-2    | b |
| 2 | 5142   | $a_0$ |
| 3 | 5940   | $a_0, a_2$ |
| 4 | 5939   | $a_0, a_3$ |
| 5 | 5933   | $a_0, a_1, a_2$ |
|   | 1210   | $a_0, a_1, a_2$ |
|   | 16990  | $a_0, a_1, a_2$ |
| 6 | 170018 | $a_0, a_3, a_4$ |

Isolated filaments of the flagellar antigens, which may be obtained by shaking, homogenization and subsequent centrifugation (R. Ansorg, W. Schmitt, Med. Microbiol. Immunol. (1980) 168: 217–226), are comprised of flagella and flagella fractions, united in a complex comprised of lipopolysaccharides (LPS) and impurities from the nutrient medium; such preparations by their nature are pyrogenic and not suited for an application on man.

In PCT patent application published under WO 86/03974 there is described the structure of polydisperse native Pseudomonas flagellar (H) antigens (FAg) obtained in accordance with a purification method, which antigens are free from pyrogenic substances. They consist of monomeric components, each monomeric component (a) containing the following amino acids: aspartic acid or asparagine (Asp/Asn), threonine (Thr), serine (Ser), glutamic acid or glutamine (Glu/Gln), glycine (Gly), alanine (Ala), valine (Val), isoleucine (Ile), leucine (Leu), thyrosine (Tyr), phenylalanine (Phe), lysine (Lys), arginine (Arg), and possibly tryptophane (Trp), (b) having the N-terminal amino acid sequence Ala-Leu-Thr-Val-Asn-Thr-Asn-Ile-Ala-, (c) having a molecular weight of from 43,500 to 53,050 and (d) being free from proline (Pro), methionine (Met), semicystine ($\frac{1}{2}$ Cys) and hystidine (His).

Moreover, the individual flagellar (H) antigen types are characterized in that the monomeric forms contain the amino acids: asparagin/aspartic acid, threonine, serine, glutamine/glutamic acid, glycine, alanine, valine, isoleucine, leucine, tyrosine, phenylalanine, lysine and arginine at certain ratios to each other. These ratios and the molecular weights of the monomeric flagellar (H) antigens are listed in Table 2.

TABLE 2

| | Number A.A./Molecule Flagellin Strains with associated H-serotype | | | | | |
|---|---|---|---|---|---|---|
| Amino acids | 170018 | 5939 | 5142 | M-2 | 1210 | 5940 |
| Aspartic acid | 64 | 69 | 74 | 74 | 76 | 68 |
| Threonine | 33 | 35 | 50 | 48 | 44 | 41 |
| Serine | 35 | 38 | 49 | 48 | 40 | 37 |
| Glutamic acid | 42 | 44 | 49 | 49 | 52 | 46 |
| Glycine | 44 | 47 | 49 | 51 | 50 | 44 |
| Alanine | 68 | 73 | 89 | 91 | 81 | 73 |
| Valine | 29 | 30 | 37 | 38 | 32 | 29 |
| Isoleucine | 29 | 30 | 29 | 30 | 32 | 29 |
| Leucine | 37 | 60 | 44 | 43 | 41 | 37 |
| Tyrosine | 3 | 3 | 5 | 4 | 4 | 3 |
| Phenylalanine | 10 | 12 | 14 | 13 | 12 | 10 |
| Lysine | 19 | 21 | 17 | 18 | 20 | 16 |
| Arginine | 15 | 16 | 16 | 18 | 18 | 16 |
| $\Sigma =$ | 450 | 478 | 522 | 525 | 502 | 449 |
| MW = | 43,500 | 46,700 | 52,720 | 53,050 | 51,250 | 45,900 |

In accordance with PCT patent application published under WO 86/03974, for obtaining the polydisperse native *Pseudomonas aeruginosa* flagellar (H) antigens, bacterial cultures are started to grow in minimum medium and are thereafter treated with a detergent, whereupon the flagellar (H) antigens are separated from the culture. Therein, the bacterial culture can either be disintegrated and subjected to a shearing process before it is treated with the detergent, or it can be subjected to the shearing forces in the presence of the detergent. The addition of the detergent makes the antigen separable from the bacterial mass; the antigens, then in solution, can be separated.

Subsequently, the antigens, separated from the bacterial mass as described above, can be freed from contaminations adhering thereto, such as lipopolysaccharides, nucleic acids, salts, polysaccharides and others, by a chromatographic purification. The detergent still present can be removed by a further purification step through chromatography on a column.

Sofar it was not known, whether these antigens have a protective effect or not. It has now been found that all the flagellar (H) antigens of the types described in PCT patent application WO 86/03974 have a protective effect, so that it is possible to produce or make available monovalent and polyvalent vaccines. This is the very object of the present invention.

In particular, it is an object of the invention to make possible an active immunoprophylaxis against infections with *Pseudomonas aeruginosa*, in particular for groups of persons that run a high risk of suffering from burns, e.g. the members of fire brigades or military personnel, or patients to be treated with immunosuppressing drugs.

It is a further object of the invention to make available immunoglobulin-G-containing preparations, which are suited for a passive immunization against *Pseudomonas aeruginosa* infections.

The vaccines of the invention are characterized in that they contain protective flagellar (H) antigens of the serotype a and b, respectively, which consist of monomeric components, each monomeric component (a) containing the following amino acids: (Asp), threonine (Thr), serine (Ser), glutamic acid (Glu), glycine (Gly), alanine (Ala), valine (Val), isoleucine (Ile), leucine (Leu), tyrosine (Tyr), phenylalanine (Phe), lysine (Lys), arginine (Arg), and possibly tryptophane (Trp) and methionine (Met), (b) having the N-terminal amino acid sequence alanine (Ala)—leucine (Leu)—threonine (Thr)—valine (Val)—asparagine (Asn)—threonine (Thr)—asparagine (Asn)—isoleucine (Ile)—alanine (Ala), (c) having a molecular weight of from 43,500 to 53,050 and (d) being free from proline, semi-cystine and histidine, and that they are free from pyrogenic substances.

In detail, according to the invention six specific H-serotypes are characterized as components of vaccines, namely the flagellar (H) antigen of the H-serotype $a_0, a_3, a_4$, whose monomeric form contains the amino acids: aspartic acid, threonine, serine, glutamic acid, glycine, alanine, valine, isoleucine, leucine, tyrosine, phenylalanine, lysine and arginine at a ratio of 64:33:35:42:44:68:29:29:37:3:10:19:15 and has a molecular weight of 43,500;

the flagellar (H) antigen of the H-serotype $a_0, a_3$, whose monomeric form contains the amino acids: aspartic acid, threonine, serine, glutamic acid, glycine, alanine, valine, isoleucine, leucine, tyrosine, phenylalanine, lysine and arginine at a ratio of 69:35:38:44:47:73:30:30:60:3:12:21:16 and has a molecular weight of 46,700;

the flagellar (H) antigen of the H-serotype $a_0$, whose monomeric form contains the amino acids: aspartic acid, threonine, serine, glutamic acid, glycine, alanine, valine, isoleucine, leucine, tyrosine, phenylalanine, lysine and arginine at a ratio of 74:50:49:49:49:89:37:29:44:5:14:17:16 and has a molecular weight of 52,720;

the flagellar (H) antigen of the H-serotype b, whose monomeric form contains the amino acids: aspartic acid, threonine, serine, glutamic acid, glycine, alanine, valine, isoleucine, leucine, tyrosine, phenylalanine, lysine and arginine at a ratio of 74:48:48:49:51:91:38:30:43:4:13:18:18 and has a molecular weight of 53,050;

the flagellar (H) antigen of the H-serotype $a_0, a_1, a_2$, whose monomeric form contains the amino acids: aspartic acid, threonine, serine, glutamic acid, glycine, alanine, valine, isoleucine, leucine, tyrosine, phenylalanine, lysine and arginine at a ratio of 76:44:40:52:50:81:32:32:41:4:12:20:18 and has a molecular weight of 51,250;

the flagellar (H) antigen of the H-serotype $a_0, a_2$, whose monomeric form contains the amino acids: aspartic acid, threonine, serine, glutamic acid, glycine, alanine, valine, isoleucine, leucine, tyrosine, phenylalanine, lysine and arginine at a ratio of 68:41:37:46:44:73:29:29:37:3:10:16:16 and has a molecular weight of 45,900.

A method of producing the vaccines of the invention is characterized in that a flagellar (H) antigen obtained from cultures of *Pseudomonas aeruginosa* and purified is sterile filtered, optionally mixed with an adjuvant, such as $Al(OH)_3$ and, if desired, admixed with a preservant, such as merthiolate.

The invention further comprises immunoglobulin-G-containing preparations active against bacterium *Pseudomonas aeruginosa* infections for prophylactic and therapeutic application, which are characterized in that they contain flagellar (H) antibodies obtained from the blood plasma of human donors or mammals immunized with protective flagellar (H) antigens.

These flagellar (H) antibodies have a motility inhibiting effect as well as the capability of an increased phagocytosis and an increased intracellular killing of *Pseudomonas aeruginosa* bacteria.

According to preferred embodiments, these immunoglobulin-G-containing preparations active against bacterium *Pseudomonas aeruginosa* infections can be produced in that plasma of human donors or mammals that have been immunized with protective flagellar (H) antigens is treated with protein precipitating agents, such as ammonium sulfate, the precipitated immunoglobulin-G-containing fraction is dissolved and purified, the purification of the immunoglobulin-G-containing fraction being advantageously carried out by passing the solution over a carrier medium to which purified flagellar antigen is covalently bound in monomeric or polymeric form, the flagella specific antibodies are eluted from the gel by pH change or chaotropic agents, such as $NH_4SCN$, and formulated into a galenic preparation.

The invention will now be explained in more detail by the following Examples, Examples 1 to 3 illustrating the production of vaccines and Example 4 illustrating the production of immunoglobulin-G-containing preparations.

EXAMPLE 1

Vaccine formulation for a *Pseudomonas aeruginosa* M-2 flagella vaccine

A flagella solution obtained from a bacterium *Pseudomonas aeruginosa* M-2 culture and purified in the manner as described above by detergent treatment, shearing and chromatographic treatment, was adjusted to a protein concentration of 100 µg/ml with distilled pyrogen-free water and made isotonic by the addition of solid sodium chloride and merthiolate (final concentration 0.9 % NaCl and 0.01 % merthiolate). Subsequently, the solution was sterile filtered through Sartorius disposable filter (0.2 µm).

After protein determination of the sterile filtered sample the flagella suspension was adjusted to 25 µg protein/ml with sterile NaCl-merthiolate solution (0.9 %/0.01 %) and subsequently was diluted to 20 µg protein/ml by addition of a 1% aluminum hydroxide suspension in sterile NaCl-/merthiolate solution.

The vaccine completed with adjuncts contained per ml:
20 µg flagella protein
2 mg $Al(OH)_3$
9 mg NaCl
0.1 mg merthiolate.

EXAMPLE 2

Vaccine formulation for a *Pseudomonas aeruginosa* 1210 flagella vaccine

A flagella solution obtained from a bacterium *Pseudomonas aeruginosa* 1210 culture and purified in the manner as described above by detergent treatment, shearing and chromatographic treatment, was adjusted to a protein concentration of 100 μg/ml with distilled pyrogen-free water and made isotonic by the addition of solid sodium chloride and merthiolate (final concentration 0.9 % NaCl and 0.01 % merthiolate). Subsequently, the solution was sterile filtered through Sartorius disposable filter (0.2 μm).

After protein determination of the sterile filtered sample the flagella suspension was adjusted to 25 μg protein/ml with sterile NaCl-merthiolate solution (0.9 %/0.01 %) and subsequently was diluted to 20 μg protein/ml by addition of a 1% aluminum hydroxide suspension in sterile NaCl-/merthiolate solution.

The vaccine completed with adjuncts thus contained per ml:
20 μg flagella protein
2 mg Al(OH)$_3$
9 mg NaCl
0.1 mg merthiolate.

EXAMPLE 3

Vaccine formulation for a *Pseudomonas aeruginosa* polyvalent flagella vaccine

Flagella solutions obtained from bacteria *Pseudomonas aeruginosa* cultures of the types M-2, 1210, 5142, 5939, 5940 and 170018 and purified in the manner as described above by detergent treatment, shearing and chromatographic treatment, were adjusted to a protein concentration of 100 μg/ml each with distilled pyrogen-free water, mixed at equal proportions and made isotonic by the addition of solid sodium chloride and merthiolate (final concentration 0.9 % NaCl and 0.01 % merthiolate). Subsequently, sterile filtering through Sartorius disposable filter (0.2 μm) was carried out.

After protein determination of the sterile filtered sample the flagella suspension was adjusted to 25 μg protein/ml with sterile NaCl-merthiolate solution (0 9 %/0.01 %) and subsequently was diluted to 20 μg protein/ml by addition of a 1% aluminum hydroxide suspension in sterile NaCl-/merthiolate solution.

The vaccine completed with adjuncts thus contained per ml:
20 μg flagella protein
2 mg Al(OH)$_3$
9 mg NaCl
0.1 mg merthiolate.

EXAMPLE 4

Pyrogen test

Vaccines prepared in the above described manner were tested for their freedom from pyrogenic components. The principle of the test consists in that, after i.v. injection of the product in three or more healthy, adult rabbits, the temperature thereof is measured for three hours (Eur. Ph., 2nd ed., 1980, Part 1, V.2.1.4); the maximum rise in temperature is recorded for each rabbit and is taken as a measure for the pyrogenicity of the product.

For carrying out the test the following was used: thermodes (Cu-constantan, thermocouples for rabbits, PhSchenk); temperature recorder (six color point printer type STD 62A, measurement range 36° to 42° C., measuring accuracy ±0.08° C.); sterile pyrogen-free injection syringes of synthetic material; sterile, pyrogen-free injection needles; steel pyrogen test box with neck fixation; scales for six pyrogen test boxes; water bath with thermostate; thermometer; scales: Sauter ES 120.

The test animals used were healthy, adult rabbits of both sexes which had a weight of at least 1,500 g, were fed with a highly nutritions standard diet free from antibiotics and showed no drop in weight during the weeks preceding the test.

The sample used was a M-2 flagella vaccine without adjuncts, which was heated to about 38° C. prior to injection. The test was carried out with a group of three rabbits, which were brought into the pyrogen test boxes at least 90 minutes before beginning of the test.

For each rabbit an initial temperature was determined on the basis of the mean value of two temperature measurements taken at intervals of 30 minutes and within the range of 40 minutes prior to administration of the test solution; rabbits that showed a temperature variation of more than 0.2° C., between two subsequent measurements, during the determination of the initial temperature, were not used for the subsequent test. Only such rabbits were used for the test whose initial temperature did not vary by more than 0.1° C. None of the rabbits that had an initial temperature higher than 39.8° C. or lower than 38° C. were used in the principal test. 1 ml of the sample per kg body weight were slowly injected into the marginal ear vein of each rabbit. The injection lasted at most 4 minutes. For each rabbit a maximum temperature was determined on the basis of the highest temperature recorded three hours after injection. The temperature of each rabbit was recorded at intervals of at most 30 minutes, starting at least 90 minutes prior to administration of the test substance and ending three hours after injection. The difference between the initial temperature and the maximum temperature of each rabbit was taken as the result. Negative differences were valued as zero.

Evaluation:

For evaluation, the temperature differences were totalled. In a group of three rabbits, the sample complies with the requirements, if the total of the individual values is smaller than 1.15° C. If the total is greater than 2.65° C., the sample does not meet the requirements.

In the case of results lying between the two above values the test must be repeated as described above. A maximum of three repetitions was carried out.

For an evaluation after repetitions all the tested animals (3, 6, 9 or a maximum of 12) were used. The test criteria are contained in the following table:

| Number of rabbits | The substance meets the test for freedom from pyrogen, if the total of the individual values is smaller than | The substance does not meet the test, if the total of the individual values is greater than |
|---|---|---|
| 3 | 1.15° | 2.65° |
| 6 | 2.80° | 4.30° |
| 9 | 4.45° | 5.59° |
| 12 | 6.60° | 6.60° |

The sample meets the test requirements, if the total of the three individual values is smaller than 1.15° C., or, in the case of repetition, meets the conditions listed in the above Table.

The results obtained with the M-2 flagella vaccine tested after injection of 1 ml/kg rabbit with individual Δt values of three rabbits were the following.

| Vaccine concentration | | |
|---|---|---|
| 10 μg/ml | 0.1° 0.1° 0.3° | ΣΔt 0.5° C. |
| 10 μg/ml | 0.3° 0.4° 0.2° | ΣΔt 0.9° C. |
| 20 μg/ml | 0.3° 0.5° 0.2° | ΣΔt 1.0° C. |
| 20 μg/ml | 0.2° 0.1° 0.2° | ΣΔt 0.5° C. |
| 20 μg/ml | 0.1° 0.4° 0.2° | ΣΔt 0.7° C. |

The preparation tested, thus, is to be considered as being free from pyrogenic substances.

EXAMPLE 5

Isolation of the IgG fraction from mouse hyperimmune plasma for use in passive immunization Plasma of mice immunized with protecive flagellar (H) antigen of the type M-2 was collected, heated for 30 minutes at 56° C. with shaking, in order to precipitate fibrin. After centrifuging for 30 minutes at 10,000 x g, a precipitation was carried out by the addition of solid ammonium sulfate to a concentration of 25 % (w/v). The suspension was stirred for 20 minutes and left standing at room temperature for 1 hour. Thereupon, the suspension was centrifuged for 30 minutes at 10,000×g and washed once with saturated ammonium sulfate solution. The precipitate was dissolved in 10 mM Na phosphate buffer, pH 7.5, 50 mM NaCl and subsequently dialyzed against this buffer overnight. After centrifugation, an ion exchange chromatography (DE-52 cellulose (Whatman)) was carried out. The passed volume contained immunoglobulin-G (IgG). After testing for IgG the solution was concentrated to the initial volume with an amicon cell and dialyzed, overnight, against a 0.9 % NaCl solution. Subsequently, a gel chromatography with Sephadex G-200 was carried out. The IgG positive fractions were concentrated to the initial volume while using an amicon cell.

This method represents a modification of the method described by D. M. Weir in Edition Handbook of Experimental Immunology, 3rd edition 1978, Chapters VII, VIII.

For the production of immunoglobulins monospecifically active against flagellar antigens of the bacterium Pseudomonas aeruginosa, also other known methods, apart from ammonium sulfate precipitation, can be used, e.g. DEAE chromatography, protein A affinity chromatography or combined methods known to the skilled artisan. The immunoglobulin-G-preparations n be further purified to monospecific immunoglobulins by employing techniques of immunoaffinity chromatography.

For the preparation of the monospecific immunoglobulins a carrier medium—preferably Sepharose 4B—is used as immunosorbent with advantage, purified flagellar antigen being covalently bound thereto in monomeric or polymeric form. The IgG-containing solution can thereafter be pumped over the affinity resin with a flow rate of preferably 1 to 2 column volumes per hour. After washing the resin with buffer solutions of higher ionic strengths (e.g. 0.5M NaCl) the flagella specific antibodies can be eluted from the gel by pH change or chaotropic agents (e.g. 3M $NH_4SCN$).

The efficacy of the protective antigens and antibodies of the invention is shown in the following:

The protective efficacy of antigens to be used for vaccines in accordance with the invention is shown by proving flagellar (H) antibodies in the serum of persons having suffered from an infection with Pseudomonas aeruginosa.

For determining the concentration of antiflagellar antibodies an immunoabsorbent assay, namely an enzyme linked immunoabsorbent assay (ELISA), or a radio immunoassay (RIA) is used. The highly purified flagellar (H) antigens described in accordance with the invention are depolymerized with a strong detergent, thereafter they are bound to a synthetic surface through unspecific interaction and brought into contact with samples of human serum. If antiflagellar (H) antibodies are present in the human serum, they bind specifically to the antigen immobilized on the solid phase. With the help of a labelled antihuman IgG antibody, flagellar (H) antigen-antibody complexes formed on the synthetic surface are shown.

This method lends itself easily to quantitative evaluation. Table 3 shows the results of a screening of serum samples on antibodies against various flagellar serotypes.

TABLE 3

| Flagellar (H)-antibody titers in human sera | | | | | | |
|---|---|---|---|---|---|---|
| Pseudomonas aeruginosa-strain | M2 | 1210 | 5939 | 5940 | 5142 | 170018 |
| H-serotype | b | $a_0a_1a_2$ | $a_0a_3$ | $a_0a_2$ | $a_0$ | $a_0a_3a_4$ |
| serum # | | | | | | |
| 1 | − | − | + | − | − | + |
| 2 | (+) | (+) | + + + + | + | + | + + + + |
| 3 | + + | + + + + | + + + + | + + + + | + + | + + + + |
| 4 | − | − | − | − | − | − |
| 5 | + | (+) | + + | + | − | + |
| 6 | + + | − | (+) | − | + | − |
| 7 | − | − | − | − | − | − |
| 8 | − | − | + + | − | − | + + |
| 9 | − | − | − | − | − | − |
| 10 | − | + | + | + | − | + |
| 11 | − | − | − | − | − | − |
| 12 | − | − | − | − | − | − |
| 13 | − | + | (+) | (+) | − | + + |
| 14 | + | − | − | − | + | − |

TABLE 3-continued

| Flagellar (H)-antibody titers in human sera | | | | | | |
|---|---|---|---|---|---|---|
| Pseudomonas aeruginosa-strain | M2 | 1210 | 5939 | 5940 | 5142 | 170018 |
| H-serotype | b | a0a1a2 | a0a3 | a0a2 | a0 | a0a3a4 |
| 15 | + | + | + | + | + | ++ |

−no antibody detectable
++titer >1:100
+++titer >1:300
(+) slightly above detection limit
+++titer >1:200
+titer >1:20 >1:100

The immunogenicity of native *Pseudomonas aeruginosa* flagellar (H) antigens is demonstrated by the results listed in Table 3 on the detection of flagellar (H) antibodies in sera of randomly selected donors.

Antibodies initiate, in various ways, the fight of foreign organisms that have invaded the body. Along with the humoral defense system (complement system) foreign organisms recognized by antibodies are killed in a sequence of reactions by lysis. Moreover, antibodies bound to the foreign organism, in cooperation with components of the complement system, can induce the take-up (phagocytosis) of the foreign organism into the defense cells of the immune system (e.g. granulocytes). In the interior of the granulocytes the phagocyted foreign cell is usually killed.

In the case of flagellated bacteria a protective effect of antibodies directed against the cell's locomotive system can also be due to the inhibition of motility and, thus, to the propagation of a focus of infection.

The inhibition of motility by flagellar (H) antibodies can be demonstrated by using flagellar (H) antigens of the serotypes listed in Table 1 for immunizing mice and by employing the thus obtained antiflagellar (H) serum in motility inhibition assays. Filter paper rings soaked with antiserum are placed on motility agar plates and the agar is inoculated with a suspension of the homologous Pseudomonas strain within these rings. The cell quantity becoming visible outside of the filter paper ring after 24 hours of incubation serves for assessing the inhibition of motility. The results of Table 4 show that mouse antisera obtained with flagellar (H) antigens inhibit the motility of the homologous Pseudomonas bacterium strain.

TABLE 4

| Motility inhibition with different amounts of homologous antiflagella serum | | | | |
|---|---|---|---|---|
| | homologous antiflagella serum ($\mu$l serum/$\mu$l pathogen suspension*) | | | |
| Strain | 30/5 | 20/10 | 10/10 | 5/10 |
| M-2 | − | − | +− | +− |
| 1210 | − | + | + | + |
| 5939 | − | − | − | − |

TABLE 4-continued

| Motility inhibition with different amounts of homologous antiflagella serum | | | | |
|---|---|---|---|---|
| | homologous antiflagella serum ($\mu$l serum/$\mu$l pathogen suspension*) | | | |
| Strain | 30/5 | 20/10 | 10/10 | 5/10 |
| 5940 | − | − | − | − |
| 5142 | − | +− | +− | +− |
| 170018 | − | +− | +− | +− |

*pathogen suspension $10^3$ pathogens/ml
− no cells outside of the filter paper ring
+− cells only on some spots outside of the filter paper ring
+ slight cell growth outside of the filter paper ring
++ marked cell growth outside of the filter paper ring with normal mouse serum always marked cell growth (++)

By inhibiting the motility of the bacteria located in a focus of infection their further propagation after colonization in the body of the patient is inhibited, yet the bacteria located in the focus still remain in a position to affect the organism of the patient by release of, for instance, toxines, proteases, etc. A genuine protection against infection is safeguarded only, if the antibodies formed through active immunization lead to a rapid killing of the invading bacteria.

In the following it will be shown that flagellar (H) antibodies induce phagocytosis and intracellular killing of the homologous Pseudomonas bacterium strain.

For the phagocytosis test, a serum not listed in Table 3 (#16) as well as the sera #3 and #5 were preincubated with a nonflagellated (fla⁻) mutant of the *Pseudomonas aeruginosa* strain M-2 (Montie, T. C., D. Doyle-Huntzinger, R. C. Craven, and I. A. Holder (1982) Infect. Immun. 38, 1296–1298), in order to remove from the sera all non-flagellar-specific antibodies. Isolated human granulocytes were used for determining the intracellular killing of *Pseudomonas aeruginosa* M-2 and the isogenic, nonflagellated mutant in untreated and in preabsorbed serum. The results shown in Table 5 show that flagellar (H) antibodies induce phagocytosis and the subsequent intracellular killing of the flagellated strain of *Pseudomonas aeruginosa*, and thus have a protective effect against infections with this pathogen in the sense of the invention.

TABLE 5

| | | Phagocytosis and intracellular killing of *Pseudomonas aeruginosa* M-2 and an isogenic nonflagellated mutant | | | | | |
|---|---|---|---|---|---|---|---|
| | | intracellular Killing *Pseudomonas aeruginosa* | | M-2 Serum without granulocytes | *Pseudomonas aeruginosa* | | M-2 fla-serum without granulocytes |
| Serum # | dilution | Serum | Serum abs. | | Serum | Serum abs. | |
| 3 | 1:25 | 94% | 59% | n. determ. | 92% | 0% | n. determ. |
| | 1:100 | 52% | 24% | n. determ. | 36% | 0% | n. determ. |
| | 1:250 | 19% | 13% | n. determ. | 16% | 3% | n. determ. |
| 5 | 1:25 | 95% | 51% | 0% | 92% | 1% | 0% |
| | 1:100 | 72% | 29% | 0% | 58% | 2% | 0% |
| | 1:250 | 35% | 25% | 0% | 21% | 0% | 0% |
| 16 | 1:25 | 95% | 57% | 0% | 93% | 0% | 0% |
| | 1:100 | 78% | 24% | n. determ. | 70% | 0% | n. determ. |

TABLE 5-continued

Phagocytosis and intracellular killing of *Pseudomonas aeruginosa* M-2 and an isogenic nonflagellated mutant

| Serum # | dilution | intracellular Killing *Pseudomonas aeruginosa* Serum | | M-2 Serum without granulocytes | *Pseudomonas aeruginosa* Serum | | M-2 fla-serum without granulocytes |
|---|---|---|---|---|---|---|---|
| | | Serum | Serum abs. | | Serum | Serum abs. | |
| | 1:250 | 5% | 0% | n. determ. | 10% | 0% | n. determ. |

A direct proof of the protective effect of antigens to be used for active immunization is only possible in the animal model. In order to simulate the situations that predispose patients for Pseudomonas infections, two animal models described in literature were used: the burned mouse model (Stieritz, D. D., and I. A. Holder (1975) J. Infect. Dis. 131, 688–691) and the Endoxan model (Cryz, S. J. Jr., Fürer, E., Germanier, R. (1983) Infect. Immunity 40, 659–664).

For both models the $LD_{50}$ dose of *Pseudomonas aeruginosa* in not immunized animals was determined, in the Endoxan model the animals were immunosuppressed; in the burned mouse model a burn of defined size was set. After immunization with the flagellar (H) antigens listed in Table 6 the animals with burns and the immunosuppressed animals, respectivley, were infected with a multiple of the previously determined $LD_{50}$ pathogen number of the homologous Pseudomonas strain. Table 6 shows the multiples of the $LD_{50}$ pathogen numbers which are tolerated by 100 % of the animals immunized with the concentration of antigen indicated in the Endoxan and in the burned mouse models.

Table 7 shows the dependence of the protective effect of the M-2 flagellar antigen. In this case the animals were immunized with increasing amounts of M-2 antigen and tested in the two models. In both cases a clear dose dependence of the protective effect of the M-2 flagellar antigen used for immunization was observed.

TABLE 6

Active protection tests with *Pseudomonas aeruginosa* flagellar (H) antigens

| antigen | amount/ mouse with Al(OH)$_3$ as adjuvant | immunization days before chall. | Endoxan model × LD$_{50}$ | burned mouse model × LD$_{50}$ |
|---|---|---|---|---|
| M-2 | 1 μg | 14 | 10 | >10$^3$ |

TABLE 6-continued

Active protection tests with *Pseudomonas aeruginosa* flagellar (H) antigens

| antigen | amount/ mouse with Al(OH)$_3$ as adjuvant | immunization days before chall. | Endoxan model × LD$_{50}$ | burned mouse model × LD$_{50}$ |
|---|---|---|---|---|
| | 3 μg | 14 | 30 | >10$^4$ |
| | 3 μg | 14 + 7 | 30 | >10$^4$ |
| 1210 | 3 μg | 14 + 7 | 30 | >10$^4$ |
| M-2 + 1210 | 1.5 μg each | 14 | 10$^2$ M-2 10 1210 | >10$^4$ M-2 >10$^4$ 1210 |
| polyvalent (6 types) | 3 μg each | 14 + 7 | 10$^2$ M-2 10 1210 | 10$^4$ M-2 10$^4$ 1210 |

TABLE 7

Dose dependence of the protective effect of the M-2 flagellar (H) antigen

| Number of Challenge-pathogens (× LD$_{50}$) | 3 μg | | 1 μg | | 0.3 μg | | 0.1 μg | | 0.03 μg | | 0.01 μg | |
|---|---|---|---|---|---|---|---|---|---|---|---|---|
| | (a) | (b) | (a) | (b) | (a) | (b) | (a) | (b) | (a) | (b) | (a) | (b) |
| 10 | 100% | 80% | 89% | 90% | 100% | 90% | 89% | 40% | 100% | 60% | 70% | 78% |
| 30 | 100% | 80% | 100% | 30% | 90% | 20% | 80% | 10% | 50% | 20% | 40% | 20% |
| 100 | 80% | 60% | 90% | 20% | 90% | 10% | 90% | 0% | 100% | 0% | 30% | 20% |
| 300 | 90% | 50% | 90% | 10% | 100% | 0% | 90% | 10% | 80% | 20% | 20% | 0% |
| 1000 | 100% | 30% | 100% | 20% | 70% | 0% | 100% | 10% | 90% | 20% | 20% | 0% | number of surviving animals:
(a) Endoxan model
(b) burned mouse model

A direct proof of the protective effect of antibodies to be used for passive immunization is only possible in the animal model. In order to simulate one of the situations that predispose patients for Pseudomonas infections, the Endoxan model described in literature was used (Cryz, S. J. Jr., Fürer, E., Germanier, R. 1983: Passive Protection Against Pseudomonas aeruginosa Infection in an Experimental Leukopenic Mouse Model. Infect. Immunity 40, 659–664).

In this test the $LD_{50}$ dose of *Pseudomonas aeruginosa* pathogens in immunosuppressed animals was determined; in the experiment described here it lay at $9.5 \times 10^2$ pathogens. Two hours after the passive immunization with a mouse anti-*Pseudomonas aeruginosa* M-2 hyperimmune plasma, for which in the antibody ELISA a titer stage of 1:1,600 was determined, the immunosuppressed animals are infected with a multiple of the previously determined LD50 pathogen number of the homologous Pseudomonas strain.

Table 8 shows that passively immunized animals are protected to a 30-fold $LD_{50}$-dose of the challenge pathogen.

TABLE 8

Passive Pseudomonas-protection test

| Inoculum 2 hours before 2 infection | Endoxan model number of surviving animals after 3 days (number of animals in the test) | |
|---|---|---|
| | 0.1 ml control plasma i.v. | 0.1 ml hyperimmune plasma i.v. |
| 3 LD$_{50}$ of M-2 | 0 (10) | 9 (10) |
| 10 LD$_{50}$ of M-2 | 0 (10) | 8 (10) |
| 30 LD$_{50}$ of M-2 | 0 (10) | 6 (10) |

TABLE 8-continued

| | Passive Pseudomonas-protection test | |
|---|---|---|
| Inoculum 2 hours before 2 infection | Endoxan model number of surviving animals after 3 days (number of animals in the test) | |
| | 0.1 ml control plasma i.v. | 0.1 ml hyperimmune plasma i.v. |
| 100 LD$_{50}$ of M-2 | 0 (10) | 0 (10) |
| 300 LD$_{50}$ of M-2 | 0 (10) | 0 (10) |

What we claim is:

1. Vaccines active against *Pseudomonas aeruginosa* infections, comprising protective flagellar (H) antigens of *Pseudomonas aeruginosa* of the serotype a and b, respectively, in combination with a pharmaceutically acceptable carrier which consist of monomeric components, each monomeric component
   (a) containing the following amino acids: aspartic acid (Asp), threonine (Thr), serine (Ser), glutamic acid (Glu), glycine (Bly), alanine (Ala), valine (Val), isoleucine (Ile), leucine (Leu), tyrosine (Tyr), phenylalanine (Phe), lysine (lys), arginine (Arg), and optionally tryptophane (Trp) and methionine (Met),
   (b) having the N-terminal amino acid sequence alanine (Ala)—leucine (Leu)—threonine (Thr)—valine (Val) —asparagine (Asn)—threonine (Thr)—asparagine (Asn) —isoleucine (Ile)—alanine (Ala),
   (c) having a molecular weight of from 43,5000 to 53,050 and
   (d) being free from proline, semi-cystine and histidine, and being free from lipopolysaccharides,
said vaccines being suited for application to man.

2. Vaccines as set forth in claim 1, which contain flagellar (H) antigens of the H-serotype a$_0$, a$_3$, a$_4$, which antigens consist of monomeric components containing the amino acids: aspartic acid, threonine, serine, glutamic acid, glycine, alanine, valine, isoleucine, leucine, tyrosine, phenylalanine, lysine and arginine at a ratio of 64:33:35:42:44:68:29:29:37:3:10:19:15 and having a molecular weight of 43,500.

3. Vaccines as set forth in claim 1, which contain flagellar (H) antigens of the H-serotype a$_0$, a$_3$, which antigens consist of monomeric components containing the amino acids: aspartic acid, threonine, serine, glutamic acid, glycine, alanine, valine, isoleucine, leucine, tyrosine, phenylalanine, lysine and arginine at a ratio of 69:35:38:44:47:73:30:30:60:3:12:21:16 and having a molecular weight of 46,700.

4. Vaccines as set forth in claim 1, which contain flagellar (H) antigens of the H-serotype a$_0$, which antigens consist of monomeric components containing the amino acids: aspartic acid, threonine, serine, glutamic acid, glycine, alanine, valine, isoleucine, leucine, tyrosine, phenylalanine, lysine and arginine at a ratio of 74:50:49:49:49:89:37:29:44:5:14:17:16 and having a molecular weight of 52,720.

5. Vaccines as set forth in claim 1, which contain flagellar (H) antigens of the H-serotype b, which antigens consist of monomeric components containing the amino acids: aspartic acid, threonine, serine, glutamic acid, glycine, alanine, valine, isoleucine, leucine, tyrosine, phenylalanine, lysine and arginine at a ratio of 74:48:48:49:51:91:38:30:43:4:13:18:18 and having a molecular weight of 53,050.

6. Vaccines as set forth in claim 1, which contain flagellar (H) antigens of the H-serotype a$_0$, a$_1$, a$_2$, which antigens consist of monomeric components containing the amino acids: aspartic acid, threonine, serine, glutamic acid, glycine, alanine, valine, isoleucine, leucine, tyrosine, phenylalanine, lysine and arginine at a ratio of 76:44:40:52:50:81:32 :32:41:4:12:20:18 and having a molecular weight of 51,250.

7. Vaccines as set forth in claim 1, which contain flagellar (H) antigens of the H-serotype a$_0$, a$_2$, which antigens consist of monomeric components containing the amino acids: aspartic acid, threonine, serine, glutamic acid, glycine, alanine, valine, isoleucine, leucine, tyrosine, phenylalanine, lysine and arginine at a ration of 68:41:37:46:44:73:29:29:37:3:10:16:16 and having a molecular weight of 45,900.

* * * * *